United States Patent [19]

Piotrowski et al.

[11] Patent Number: 5,473,036
[45] Date of Patent: Dec. 5, 1995

[54] PROCESS FOR FORMING A BROMOMAGNESIUM TETRAKIS (FLUOROPHENYL) BORATE

[75] Inventors: Andrzej M. Piotrowski, Peekskill; Dennis F. Taylor, Granite Springs, both of N.Y.; Dietmar Seyferth, Lexington, Mass.

[73] Assignee: Akzo Nobel N.V., Arnhem, Netherlands

[21] Appl. No.: 398,236

[22] Filed: Mar. 3, 1995

[51] Int. Cl.$^6$ ............................................... C08G 79/08
[52] U.S. Cl. ............................................ 528/4; 568/6
[58] Field of Search ..................................... 568/6; 528/4

[56] References Cited

U.S. PATENT DOCUMENTS

| | | | |
|---|---|---|---|
| 4,894,302 | 1/1990 | Hoffman et al. | 568/6 |
| 5,296,433 | 3/1994 | Siedle et al. | 502/117 |
| 5,340,898 | 8/1994 | Cavezzan et al. | 528/19 |
| 5,362,423 | 11/1994 | Ikeda et al. | 260/665 R |
| 5,399,780 | 3/1995 | Ikeda et al. | 568/1 |
| 5,420,355 | 5/1995 | Ikeda et al. | 568/6 |

FOREIGN PATENT DOCUMENTS

| | | | |
|---|---|---|---|
| 353030 | 1/1990 | European Pat. Off. | C07F 5/02 |
| 505997 | 9/1992 | European Pat. Off. | C08F 12/04 |
| 505972 | 9/1992 | European Pat. Off. | C08F 212/04 |
| 1304302 | 1/1973 | United Kingdom | G01N 27/40 |

OTHER PUBLICATIONS

A. G. Massey et al, "Perfluorophenyl Derivatives of the Elements: I. Tris(Pentafluorophenyl)Boron", Journal of Organometallic Chemisty, 2 (1964), 245–250.

J. L. W. Pohlmann et al., "Pentafluorophenyl–Metal Chemistry II: Preparation and Characterization of Group IIIA Derivatives", Z. Naturforschg. 20b, 5–11 (1965).

Japanese Patent Abstracts, vol. 13 No. 39(C–563), abstracting Japanese Patent Publication No. 63–238087 (Oct. 1988) entitled "Novel Tetraaryl Borate", Applicant: Central Glass Co. Ltd.; Inventor: H. Kobayashi.

M. Brookhart et al., "[(3,5–$(CF_3)_2C_6H_3)_4$B+9$^-$[H$(OEt_2)_2$]$^+$: A Convenient Reagent for Generation and Stabilization of Cationic, Highly Electrophilic Organometallic Complexes", Organometallics 1992, 11, 3920–3922.

H. Nishida et al., "Tetrakis[3,5–Bis(Trifuoromethyl)Phenyl] Borate. Highly Lipophilic Stable Anionic Agent for Solvent–Extraction of Cations", Bull. Chem. Soc. Jpn. 57, 2600–2604 (1984).

Abstract in English) of International Patent Publication No. WO 94/00459 (Jan.1994) and copy of International Search Report.

Chemical Abstracts, vol. 112 (1990), 77273e.

J. C. W. Chien et al., "Isospecific Polymerization of Propylene Catalyzed by rac–Ethylenebis(indenyl)methylzirconium 'Cation'", J. Am. Chem. Soc. 113, 8570–8571 (1991).

Primary Examiner—Melvin I. Marquis
Attorney, Agent, or Firm—Richard P. Fennelly; Louis A. Morris

[57] ABSTRACT

Bromomagnesium tetrakis(fluorophenyl) borate reactible intermediates can be formed by reacting at least four equivalents of fluorophenyl magnesium bromide with every one equivalent of boron trifluoride in ether solvent using a sufficient amount of heat to drive the reaction to completion. This type of reactible intermediate can then be reacted with a salt containing a suitable cation, such as ammonium, trityl or onium, preferably substituted with phenyl or alkyl, such as lower alkyl, to form the desired combination of weakly coordinating boron anion and activating cation.

12 Claims, No Drawings

PROCESS FOR FORMING A BROMOMAGNESIUM TETRAKIS (FLUOROPHENYL) BORATE

BACKGROUND OF THE INVENTION

Combinations of an activating cation and a weakly coordinating (sometimes referred to as "non-coordinating") borate anion, such as in ammonium tetrakis(pentafluorophenyl)borates, are used as catalyst components in metallocene Ziegler-Natta catalysts. A number of procedures have been described in the prior art in regard to how the borate anion portion of such materials might be prepared.

European Patent Publication Nos. 505,972 and 505,997 show, for example, the preparation of tri(n-butyl)ammonium tetra(pentafluorophenyl)borate by the formation of pentafluorophenyllithium from bromopentafluorobenzene and butyllithium with the subsequent reaction of the pentafluorophenyllithium with trichloroboron to produce tris(pentafluorophenyl)boron. The tris(pentafluorophenyl)boron was then reacted with pentafluorophenyllithium to produce lithium tetra(pentafluorophenyl)borate which was isolated. The last step of the reaction was the reaction of lithium tetra(pentafluorophenyl)borate with tri-n-butylamine hydrochloride in water to produce the desired tri(n-butyl)ammonium tetra(pentafluorophenyl)borate.

Japanese Published Patent Application No. 63-238087 shows the preparation of a tetramethylammonium tetrakis fluoro-containing borate by use of a Grignard reagent. A similar Grignard route for the formation of sodium tetrakis(3,4-bis(trifluoromethyl)phenyl)borate is shown in Chem Abstracts, Vol. 112, 1990, 77273e.

Finally, PCT International Patent Publication No. WO94/00459 shows a process for producing tetrakis-fluorophenylborates by the reaction of boron trichloride with an alkali metal, alkaline earth metal or dialkylaluminum-substituted phenyl reagent which can contain either hydrogen or halogen on the phenyl ring.

SUMMARY OF THE INVENTION

A bromomagnesium tetrakis(fluorophenyl) borate reactible intermediate can be formed by reacting at least four equivalents of fluorophenyl magnesium bromide with every one equivalent of boron trifluoride in ether solvent using a sufficient amount of heat to drive the reaction to completion. This reactible intermediate can then be reacted with a salt containing a suitable cation, such as substituted ammonium, trityl or onium to form the desired combination of weakly coordinating boron anion and activating cation.

DESCRIPTION OF PREFERRED EMBODIMENTS

The type of bromomagnesium tetrakis (fluorophenyl) borate reactible intermediate which is the subject of the present invention has the general formula

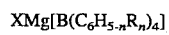

where X is halogen, such as bromo, n is an integer of from 1 to 5, preferably 5, and where R can be fluorine, trifluoromethyl, or fluorinated alkyl, such as lower alkyl of from one to about four carbon atoms. This reactible intermediate can be formed by reacting at least four equivalents of the corresponding fluorophenyl magnesium bromide with every one equivalent of boron trifluoride in ether solvent using a sufficient amount of heat to drive the reaction to completion.

The ether is needed to solubilize the Grignard reagent, fluorophenyl magnesium bromide, and is preferably a lower alkyl-group containing ether such as diethylether or dibutylether. The temperature of the heating step should be no less than about 35° C., preferably up to temperatures of about 130° C.

The foregoing type of reactible intermediate can then be reacted with a salt, such as a chloride, containing a suitable cation, such as ammonium, trityl or onium (see U.S. Pat. No. 5,340,898 at Col. 1, lines 45–60 for a definition of "onium"), to form the final combination of weakly coordinating borate anion and activating cation for use, for example, in coordination or cationic polymerization reactions (such as metallocene polymerization). Representative ammonium salts contain, as the cation portion, $R_3NH^+$, where R can be phenyl (Ph) which is either unsubstituted or substituted (e.g., with such alkyl groups as lower alkyl, namely, methyl and/or ethyl). Such ammonium salts may be exemplified by triethylammonium chloride or phenyldimethylammonium chloride. The corresponding trityl salts have a cation of the formula $Ph_3C^+$, whereas the onium salts can contain a cation of the formula $Ph_2I^+$.

The route for forming the ammonium and onium-containing products involves the reaction of the intermediate in water with the selected salt to precipitate the desired combination of weakly coordinating boron-containing anion and activating cation. The route for forming the trityl-containing products uses a hydrocarbon solvent medium (e.g., toluene) in which the byproduct salt is insoluble but the borate anion/cation is soluble.

The Examples which follow further illustrate preferred embodiments of the present invention.

EXAMPLE 1

This Example describes the preparation of triethylammonium tetrakis(pentafluorophenyl) borate.

A solution of 100 millimoles of pentafluorophenyl-magnesium bromide in 60 ml of ether was prepared using 2.8 g of magnesium and 25 grams of pentafluorophenyl bromide. Unreacted magnesium was removed by filtration, and the solution was diluted with 120 ml of dry butyl ether. This was then followed by the addition of 3.12 g of boron trifluoride etherate. The flask with the reaction mixture was then placed in an oil bath and bath temperature was increased to 128° C. over a period of one-half hour. Ether was then gradually distilled off, the reflux temperature being raised from about 37° C. to about 65° C. (temperature in the vapor space). When no more distillate was collected at bath temperature of about 128° C., more solvent was removed under reduced pressure to leave about 60 ml of liquid in the flask. Fresh butyl ether in the amount of 120 ml was then added, and the reaction mixture was stirred at room temperature for seventeen hours. The oil bath temperature was then increased to 114° C., and the reaction mixture was stirred at this temperature for a period of two hours. The solution of such prepared bromo-magnesium tetrakis-pentafluorophenyl borate was then transferred to a flask containing 10.8 g of triethylammonium chloride in 80 ml of water. After stirring for one-half hour and the usual workup, solvent was removed under reduced pressure leaving 22.42 g of crude product. Pure triethylammonium tetrakis(pentafluorophenyl) borate could be obtained by washing crude product with chloroform or by crystallization from $CH_2Cl_2$/butyl ether. The yield of pure triethylammonium tetrakis(pentafluorophenyl) borate was 13.8 g or 80.5% based on $BF_3$.

EXAMPLE 2

This Example describes the preparation of phenyldimethylammonium tetrakis(pentafluorophenyl) borate.

A solution of 104 millimoles of pentafluorophenyl-magnesium bromide in 60 ml of ether was prepared using 2.89 g of magnesium and 25.9 grams of pentafluorophenyl bromide. Unreacted magnesium (0.32 g) was removed by filtration and the solution was diluted with 130 ml of dry butyl ether. This was then followed by the addition of 3.71 g of boron trifluoride etherate. The flask with the reaction mixture was then placed in an oil bath, and the bath temperature was increased to allow gradual ether removal by distillation. About 50 ml of solvent was removed. Any residual ether was then removed by vacuum distillation leaving about 40–50 ml of liquid. (According to the literature, complete removal of the solvent may result in an explosion). Fresh butyl ether in the amount of 120 ml was then added and the reaction mixture was stirred at room temperature for seventeen hours. The oil bath temperature was then increased to 124°–128° C., and the reaction mixture was stirred at this temperature for a period of two hours. The solution of such prepared bromomagnesium tetrakispentafluorophenyl borate was then transferred to a flask containing 10.0 g of phenyldimethylammonium chloride in 50 ml of water. After stirring for one-half hour and the usual workup as described in Example 1, solvent was removed under reduced pressure leaving brown oil which crystallized after addition of $CHCl_3$ with some cyclohexane. White crystals (13.5 g) were separated by filtration. Solvent was then removed from the filtrate and 2.8 g of white crystals were separated after ether addition. The overall yield was 16.3 g of phenyldimethylammonium tetrakis(pentafluorophenyl) borate which is 77.7% based on pentafluorophenyl bromide.

The foregoing Examples are presented to illustrate certain preferred embodiments of the present invention and, for that reason, should not be construed in a limiting sense. The scope of protection that is desired is set forth in the claims which follow.

We claim:

1. A process for forming a bromomagnesium tetrakis(fluorophenyl) borate reactible intermediate by reacting at least four equivalents of fluorophenyl magnesium bromide with every one equivalent of boron trihalide in ether solvent using a sufficiently elevated temperature to drive the reaction to completion.

2. A process as claimed in claim 1 wherein the fluorophenyl is pentafluorophenyl.

3. A process as claimed in claim 1 wherein the ether is a lower alkyl ether.

4. A process as claimed in claim 1 wherein the fluorophenyl is pentafluorophenyl and the ether is a lower alkyl ether.

5. A process as claimed in claim 1 wherein the temperature is no less than about 35° C.

6. A process as claimed in claim 2 wherein the temperature is no less than about 35° C.

7. A process as claimed in claim 3 wherein the temperature is no less than about 35° C.

8. A process as claimed in claim 4 wherein the temperature is no less than about 35° C.

9. A process for forming the combination of a weakly coordinating boron-containing anion and a cationic activator for use in a coordination polymerization catalyst system which comprises reacting the bromomagnesium tetrakis(fluorophenyl) borate reactible intermediate of claim 1 with a salt comprising a cation selected from the group consisting of ammonium, trityl and onium.

10. A process as claimed in claim 9 wherein the cation is ammonium.

11. A process as claimed in claim 10 wherein the ammonium halide is triethylammonium chloride.

12. A process as claimed in claim 10 wherein the ammonium halide is phenyldimethylammonium chloride.

\* \* \* \* \*